United States Patent [19]

Yamamoto et al.

[11] Patent Number: 5,582,820
[45] Date of Patent: Dec. 10, 1996

[54] MULTILAYERED STRUCTURE AND COLOSTOMY BAG MADE THEREFROM

[75] Inventors: Yoshio Yamamoto; Tohei Moritani, both of Kurashiki; Akihiko Kawasaki, Amagasaki, all of Japan

[73] Assignee: Kuraray Co., Ltd., Kurashiki, Japan

[21] Appl. No.: 177,727

[22] Filed: Jan. 5, 1994

Related U.S. Application Data

[63] Continuation of Ser. No. 442,349, filed as PCT/JP89/00289, Mar. 17, 1989, abandoned.

[30] Foreign Application Priority Data

Mar. 18, 1988 [JP] Japan ..................... 63-66432

[51] Int. Cl.$^6$ ................ A61L 9/01; A61L 25/00
[52] U.S. Cl. ............ 424/76.6; 604/333; 428/34.3; 428/36.6; 428/36.7
[58] Field of Search ............... 424/76.5, 76.6; 604/333; 428/34.3, 36.6, 36.7

[56] References Cited

U.S. PATENT DOCUMENTS

| | | | |
|---|---|---|---|
| 3,882,259 | 5/1975 | Nohara et al. | 525/60 |
| 4,034,079 | 7/1977 | Schoonman | 424/78 |
| 4,621,014 | 11/1986 | Lu | 428/216 |

*Primary Examiner*—Edward J. Webman
*Attorney, Agent, or Firm*—Cummings & Lockwood

[57] ABSTRACT

A multilayered structure comprising at least 2 layers of a gas barrier resin layer and a protective layer, at least 1 layer thereof containing a deodorant, and a colostomy bag having excellent odor barrier properties (skatole and ammonia barrier properties) made of the film of the multilayered structure.

9 Claims, No Drawings

MULTILAYERED STRUCTURE AND COLOSTOMY BAG MADE THEREFROM

This application is a continuation of application Ser. No. 07/442,349, filed as PCT/JP89/00289 Mar. 17, 1989, now abandoned.

FIELD OF THE INVENTION

The present invention relates to a multilayered structure and colostomy bag made therefrom having excellent odor barrier properties.

BACKGROUND ART

High barrier properties against odorous materials are required for plastic films for packaging odorous wastes, such as colostomy bags and garbage bags, and plastic films for packaging fish, fruits, vegetables, and the like.

Single-layer films of low-density polyethylene, plasticized polyvinyl chloride and the like have been used for colostomy bags. However, single-layer films of low density polyethylene, plasticized polyvinyl chloride and the like, have insufficient odor barrier properties, and the odor of the contents emanates outward to cause the wearer to become uncomfortable. There is a need for a film having high odor barrier properties. The use of multilayered films comprising a barrier layer of ethylene-vinyl alcohol copolymer (hereinafter referred to as EVOH) or polyvinylidene chloride resin having odor barrier properties have been proposed. Japanese Utility Model Application Laid-open No. 175248/1985 discloses a colostomy bag comprising EVOH as a barrier layer. However, colostomy bags comprising EVOH as an odor barrier layer have not been put into practical use, because the barrier properties of EVOH against low-molecular weight amines such as ammonia are somewhat insufficient. The use of polyvinylidene resin has been disclosed, for example, in Japanese Patent Kohyo No. 501631/1982 and Japanese Patent Application Laid-open No. 137368/1985. However, commercially available colostomy bags utilizing polyvinylidene chloride are still unsatisfactory in odor barrier properties.

Japanese Patent Application Laid-open Nos. 60732/1986 and 148236/1986 disclose a plastic film containing a deodorant composed of a ferrous compound and an organic acid. Japanese Patent Application Laid-open No. 86031/1987 discloses a resin composition containing a deodorant of an organic acid, and Japanese Patent Application Laid-open Nos. 235363/1987, 235364/1987 and 235365/1987 disclose resin compositions containing deodorant composed of a zinc compound and an inorganic acid. However, the deodorizing function of deodorants has its limit and the odor of odorous materials cannot completely be barred. Further no combinations of gas barrier resin with deodorant are yet known.

DISCLOSURE OF THE INVENTION

As described above, there has been a long felt need for a material, particularly a plastic film, which will exhibit excellent barrier properties against odor components contained in odorous materials.

An odor barrier layer consisting only of a gas barrier resin has insufficient odor barrier properties, and hence cannot provide a satisfactory colostomy bag. On the other hand, deodorants, when blended in thermoplastic resins having no gas barrier properties, such as polyolefins, give colostomy bags with only insufficient odor barrier properties, which however are higher than the resins without the deodorants.

The present inventors have unexpectedly found that multilayered structures comprising at least a gas barrier resin layer and a protective layer, at least one of which, particularly the protective layer, contains a deodorant, will exhibit almost perfect odor barrier properties against most odor components. Thus, such multilayered structures are very useful as colostomy bags. The multilayered structures comprising a gas barrier resin layer and a protective layer containing a deodorant are epoch-making materials exhibiting high barrier properties against various odors, and can hence be used for many purposes aside from a colostomy bag.

Although the reason why the multilayered structure of the present invention exhibits such an excellent odor barrier property is not quite clear, it is believed that the combination of a gas barrier resin and a deodorant produces an effective barrier to various odorous components.

The invention is now described ill more detail. The gas barrier resin as used in the present invention is a resin having in its film form, an oxygen transmission rate at 20° C. and 65% RH of not more than 100 cc·20μ/m²·day·atm, and more specifically not more than 10 cc·20μ/m²·day·atm. Examples of the gas barrier resin are EVOH, polyvinyl alcohol, polyvinylidene chloride or copolymers of vinylidene chloride with other vinyl compounds, polyacrylonitrile or copolymers of acryacrylonitrile with other vinyl compounds, polyesters, gas-barrier polyesters (e.g. a polyester derived from a diol having not more than 8 carbon atoms, an acid such as 1,4-phenylenedioxydiacetic acid and terephthalic acid described in Japanese Patent Kohyo No. (501060/1984), polyamides, gas-barrier polyamides (e.g. metaxylylenediamine polyamide described in Japanese Patent Application Laid-open No. 96064/1978) and the like, among which the most preferred is EVOH.

Any EVOH can, as long as it is a hydrolyzed product of ethylene-vinyl acetate copolymer, be used in the present invention but, particularly, an having an ethylene content of 20 to 50 mol %, preferably 27 to 40 mol %, a saponification degree of the vinyl acetate units of at least 96%, preferably at least 99% and a melt index (190° C., 2160 g) of 0.2 to 60 g/10 min is most suited for the purpose of the present invention.

The EVOH in the present invention may be modified with not more than 5 mol % of a copolymerizable monomer. Examples of the copolymerizable monomer are propylene, 1-butene, 1-hexene, 4-methyl-1-pentene, acrylic acid esters, methacrylic acid esters, maleic acid, fumaric acid, itaconic acid, higher fatty acid vinyl esters, alkyl vinyl ethers, N-(2-dimethylaminoethyl)methacrylamide or quaternary compounds thereof, N-vinylimidazole or quaternary compounds thereof, N-vinylpyrrolidone, N,N-butoxymethylacrylamide, vinyltrimethoxysilane, vinyldimethylmethoxysilane, and the like.

The deodorants used in the present invention are those capable of deodorizing various odorous materials, in particular, ammonia, trimethylamine, acetaldehyde, hydrogen sulfide, methylmarcaptan, methyl sulfide, methyl disulfide, styrene, phenol, n-valeric acid, i-valeric acid and the like. There are no particular restrictions to the type of the deodorants, and typical examples of them are organic acid, iron (II) (or, ferrous) compounds, zinc compounds, aluminum compounds, silicon compounds and ferrous compound-organic acid compositions. These deodorants may either be used singly or in combination.

Examples of the zinc compound are zinc silicate, zinc oxide, zinc sulfate, zinc chloride, zinc phosphate, zinc nitrate, zinc carbonate, zinc acetate, zinc oxalate, zinc citrate zinc fumarate, zinc formate and the like.

Examples of the aluminum compound are aluminum sulfate, aluminum phosphate, aluminum silicate, aluminum potassium sulfate and the like.

Examples of the silicon compound are silica, silicon phosphoric acid compounds such as silicon o-phosphate, silicon pyrophosphate-I and silicon pyrophosphate-II, activated silica gel and the like.

Any compound capable of forming ferrous ions can be used as the ferrous compound and examples of them are inorganic acid salts of Fe (II) such as ferrous sulfate, ferrous chloride, ferrous nitrate, ferrous bromide, ferrous iodide; and organic acid salts of Fe (II) such as ferrous gallate, ferrous malate and ferrous fumarate; among which ferrous sulfate and ferrous chloride are preferred.

Compositions of zinc compounds and silicon compounds may also be used preferably. The preferred example of the composition is a substantially amorphous particulate zinc silicate with the ratio by weight of zinc oxide to silica of from 1:5 to 5:1, more preferably from 1:4 to 4:1 and most preferably from 1:3 to 3:1.

Compositions of zinc compounds and aluminum compounds may also be used preferably. The preferred example is a mixture of zinc oxide and/or zinc carbonate with aluminum sulfate and/or aluminum potassium sulfate, wherein the aluminum compound is used in an amount of 1 to 1,000 parts by weight based on 100 parts by weight of the zinc compound, preferably 30 to 300 parts by weight on the same basis.

The preferred organic acids are organic acids having at least 8 carbon atoms, such as aliphatic monocarboxylic acids, aliphatic polycarboxylic acids, aromatic monocarboxylic acids and aromatic polycarboxylic acids, among which particularly preferred is aromatic polycarboxylic acids. Examples of the aromatic polycarboxylic acid are phthalic acid, terephthalic acid, isophthalic acid, trimellitic acid, 1,2,3-benzenetricarboxylic acid, 1,3,5-benzenetricarboxylic acid, pyromellitic acid, benzenehexacarboxylic acid, naphthalenedicarboxylic acid, naphthalenetricarboxylic acid, naphthalenetetracarboxylic acid, diphenyltetracarboxylic acid, diphenyl ether tetracarboxylic acid, azobenzenetetracarboxylic acid, and anhydrides of the foregoing. Among the above, particularly preferred is benzenetricarboxylic acid and, still more preferred is trimellitic acid.

Any compound capable of forming ferrous ion can, same as for the afore-described ferrous compound, be used as the ferrous compound used for the ferrous compound-organic acid composition. Examples of the compound are inorganic acid salts of Fe (II) such as ferrous sulfate, ferrous chloride, ferrous nitrate, ferrous bromide, ferrous iodide; and organic acid salts of Fe (II) such as ferrous gallate, ferrous malate and ferrous fumarate; among which ferrous sulfate and ferrous chloride are preferred.

Any organic acid which is soluble in water may be used for the ferrous compound-organic acid composition. Examples of the organic acid are ascorbic acids such as ascorbic acid, isoascorbic acid and metal salts thereof, and carboxylic acids such as citric acid, isocitric acid, lactic acid, tartaric acid and malic acid, among which preferred is L-ascorbic acid.

The ferrous compound-organic acid compositions used in the present invention preferably contain the two components chemically bonded to each other. Such compounds can for example be prepared by first mixing and dissolving the two components in water, then drying and pulverizing the aqueous solution by spray drying, lyophilization or any like method. The ratio by weight of the ferrous compound and the organic acid is preferably in the range of from 1:0.01 to 1.0 and more preferably in the range of from 1:0.02 to 0.80. Where the organic acid is an ascorbic acid, the ratio by weight of the ferrous compound and the ascorbic acid is preferably in the range of from 1:0.02 to 0.30, more preferably in the range of from 1:0.02 to 0.13 and most preferably in the range of from 1:0.05 to 0.13. In the present invention the ferrous compound-organic acid composition may contain 2 or more ferrous compounds or 2 or more organic acids. Furthermore, the composition may preferably comprise as a stabilizer for the deodorizing function 2 to 20% by weight of alum based on the total weight of the ferrous compound and organic acid. Any alum can be used but, preferably used are potassium alum, ammonium alum and sodium alum.

Also used are other deodorants, e.g. compositions of stabilized metal compounds, such as those comprising zinc compounds and polycarbozylic acids; enzyme-model compounds, such as Fe (III)—phthalocyanine derivatives; saps or extracts from paulownia, holly, sweet osmanthus, butterbur, lilac, forsythia, chestnut, alder the like; aluminosilicates such as zeolite; clay minerals of magnesium silicate hydrates, such as sepiolite, cryolite, varigorskite and laphrinite; activated humic acid; activated alumina; activated charcoal and the like.

Particularly preferred among the above-mentioned deodorants are zinc compounds such as zinc oxide and zinc sulfate; silicon compounds such as silica and silicon orthophosphate; aluminum compounds such as aluminum sulfate and aluminum postassium sulfate; compositions of zinc compounds and silicon compounds; organic acids; and ferrous compound-organic acid compositions.

Among the above deodorants, zinc silicate, zinc oxide and alums can adequately be incorporated in gas barrier resins, particularly in EVOH.

In the present invention, while the deodorant is most preferably contained in a protective layer, particularly in a protective layer comprising a thermoplastic resin, in some cases the deodorant carefully selected may be incorporated in a gas barrier layer to exhibit well the deodorizing function. Furthermore, where in the multilayered structures of the present invention an adhesive layer is provided between a gas barrier layer and a protective layer, particularly a thermoplastic layer, the deodorant may also be incorporated in the adhesive layer. The deodorant may be incorporated in one of the layers constituting the multilayered structure, or may, as required, be incorporated into two or more layers. The amount of the deodorant incorporated is at least 0.1% by weight based on the weight of the layer incorporating it, preferably in the range of from 0.2 to 50% by weight on the same basis, and more preferably in the range of from 0.5 to 10% by weight on the same basis. With incorporation of amounts less than 0.1% by weight, the synergetic effect obtained in combination with a gas barrier resin for odor barrier properties will be insufficient.

In the present invention, the deodorants are incorporated into a material constituting a protective layer by various methods. Where the protective layer is a thermoplastic resin layer, the applicable methods are one which comprises blending the deodorant into the thermoplastic resin beforehand using a single-screw or twin-screw extruder, Brabender Plastograph, or the like; one which comprises directly feeding the deodorant to a forming machine and conduct formation while kneading it with the resin in the machine; one which comprises preparing high-concentration master pellets by using an extruder, diluting the pellets to about 1/10 the original concentration, followed by melt extrusion; one which comprises mixing the deodorant, particularly in its powder form, into a solution of the thermoplastic resin and then forming the mixture by casting; and the like. Where the protective layer is paper, nonwoven fabric or woven fabric, the deodorant may be incorporated into the layer by dipping, coating or like methods.

The deodorant may also be incorporated into a gas barrier resin or into an adhesive resin by methods similar to those employed for the incorporation into the thermoplastic resin.

The "protective layer" as referred to in the present invention is a layer which provides the gas barrier layer with high strength, flexibility, higher moisture-proofness and heatsealability, and further with a high odor barrier property by the incorporation of a deodorant into said protective layers. Examples of protective layers are thermoplastic resin layer, particularly hydrophobic thermoplastic resin layers, paper, nonwoven fabric, woven fabric and the like.

There are no particular restrictions with respect to the thermoplastic resin used for the protective layer in the present invention but, preferably used are thermoplastic resins with high heatsealability, e.g. polyolefins such as low density polyethylene, high density polyethylene, linear low density polyethylene, polypropylene, ethylene-propylene copolymer and polybutene, copolymers principally containing an olefin such as ethylene-vinyl acetate copolymer and ethylene-ethyl acrylate copolymer and ionomers, and the like. Polyethylene terephthalate, polycarbonates, polyamides, polystyrene, polyvinyl chloride and the like may also be used. In the case where polyethylene terephthalate or a polyamide is used as the gas barrier resin, the thermoplastic resin is preferably selected from resins having different characteristics than the polyethylene terephthalate or polyamide, for example a resin with higher sealability or a resin with higher flexibility.

In the multilayered structure of the present invention, there is no particular restriction to the relative locations of the deodorant-containing layer and the gas barrier resin layer but, it is preferred that the protective layer containing a deodorant be provided outwardly relative to the gas barrier resin layer and more apart from the contents generating odors.

Thus, examples of the preferred construction of the protective layer, P, the gas barrier resin layer, G, and a deodorant, D, are (P containing D/G), (P containing D/G/P containing D), (P containing D/G/P), (P/G containing D), (P/G containing D), (P/G containing, D/P), (P containing D/G containing D), (P containing D/G containing D/P), (P containing D/G containing D/P containing D), and others, among which (P containing D/G/P containing D) is the best. P, G, or (P containing D) or (G containing D) may comprise 2 or more layers. Besides, an adhesive layer may suitably be provided between each layer as hereinafter described, and in this case a deodorant may either be incorporated only in the adhesive layer or in both the adhesive layer and in P and/or G.

There are no specific restrictions with respect to thickness construction of the multilayered structure of the present invention but, generally, the thicknesses of the gas barrier resin layer and the protective layer containing deodorant are 3 to 50µ, preferably 5 to 30µ and 5 to 300µ, preferably 5 to 150µ respectively, with the total thickness being 20 to 500µ, preferably 60 to 200µ.

The multilayered structure of the present invention can be produced by co-extrusion, extrusion lamination, dry lamination, sandwich lamination or like processes.

Where, in the multilayered structure of the present invention, the interlayer bond strength between the gas barrier resin layer and the protective layer, particularly the protective layer containing a deodorant, is not so high, it is preferred that an adhesive be used or an adhesive resin layer be provided between the two layers. Any adhesive resin may be used with no particular limitation as long as it does not cause delamination during use but, where a co-extrusion process is employed for the preparation of the multilayered structure, the preferred adhesive resins are polyolefins such as polyethylene, ethylene-α-olefin copolymers, ethylene-vinyl acetate copolymers having a vinyl acetate content of not more than 45% by weight, and modified polyolefins obtained by chemically bonding (e.g. by addition reaction, grafting, and the like) an ethylenically unsaturated carboxylic acid or hydrides thereof to ethylene-acrylic acid ester or methacrylic acid ester copolymers having an acrylic acid ester or methacrylic acid ester content of not more than 45% by weight). These adhesive resins may be provided, as well as between the two layers, by incorporation into either one or both of the two layers.

In some cases, high flexibility is required for the multilayered structure of the present invention. For example, films for colostomy bags are required to be flexible, thereby preventing unsatisfactory feeling when the film touches the wearer's skin and generation of sound due to bending or abrasion of the film when worn, which sound will disclose the fact that the user wears the bag to other people. In some other cases, where the films are subjected to vibration or bending during use, high resistance to generation of pinholes is required for the films. In such cases, a more flexible resin may be blended to the gas barrier resin or another monomer may be copolymerized to provide high flexibility. Where EVOH is used as the gas barrier resin, it is preferred to blend with the EVOH an ethylene copolymer resin containing 2 to 25 mol % of at least one component selected from the group consisting of vinyl acetate, acrylic acid esters and methacrylic acid esters (hereinafter such ethylene copolymer is referred to as "blended resin"), which blending improves flexibility. The comonomer being contained in the blended resin in an amount of 2 mol % or less will be short of effectively of improving the flexibility of EVOH, while that in an amount exceeding 25 mol % will render the blend composition with EVOH insufficient in thermal stability, thereby generating gelled matter in the blend layer. Examples of the acrylate to be copolymerized with ethylene include, among others, methyl acrylate, ethyl acrylate, propyl acrylate, butyl acrylate, 2-ethylhexyl acrylate, dodecyl acrylate and eicosyl acrylate, among which preferred are methyl acrylate and ethyl acrylate, ethyl acrylate being the most preferred. Examples of the methacrylate to be copolymerized with ethylene include, among others, methyl methacrylate, ethyl methacrylate, propyl methacrylate, butyl methacrylate, 2-ethylhexyl methacrylate, dodecyl methacrylate and aicosyl methacrylate, among which preferred are methyl methacrylate and ethyl methacrylate, ethyl methacrylate being the most preferred. These comonomers may be used in combination. Also, a third comonomer may be used as long as it does not impair the flexibility. Furthermore, two or more copolymers of the ethylene-vinyl acetate copolymer, ethylene-acrylate copolymer or ethylene-methacrylate copolymer may at the same time be blended with EVOH. The blending ratio of EVOH and blended resin may optionally be selected; and the more EVOH, the better the odor barrier-property and gas barrier property will be, while the more the blended resin, the better the flexibility. The preferred blending ratio well balancing the odor barrier property and gas barrier property, and flexibility is within the range of 60 to 95 parts by weight of EVOH and 40 to 5 parts by weight of the blended resin, and more preferably within the range of 65 to 80 parts by weight of EVOH and 35 to 20 parts by weight of the blended resin. EVOH and the blended resin is blended by using a Banbury mixer, a single-screw or twin-screw extruder, a Branbender Plastograph or the like. Each of the two polymers may directly be fed to a forming machine, where they are then kneaded and formed. When blending the resins, other additives, (e.g. various resins, thermal stabilizers, antioxidants, plasticizers, colors, and the like) may also be added within a limit not to detract from the effect and function of the present invention. Examples of the thermal stabilizers used are hydrotalcites, metal soaps, lead compounds, hindered amines, sulfides and phosphite, among which hydrotalcites are particularly effective. The above-mentioned additives can also be used when EVOH is not blended with the blended resin.

Where the film of the multilayered structure of the present invention is used for a colostomy bag or the like which requires flexibility, it is preferred that, besides the above-mentioned incorporation of the blended resin into the gas barrier resin to provide flexibility, the protective layer be laminated with the gas barrier resin layer, in particular that containing a deodorant be a thermoplastic resin layer having a Young's modulus at 20° C. of 2.5 kg/mm$^2$ or below, more specifically of 0.1 to 2 kg/mm$^2$. The term Young's modulus, of the protective layer herein, means the Young's modulus exhibited by the resin constituting the protective layer and measured at 20° C., 65% RH according to ASTM D-882-67. Examples of thermoplastic resins giving the above-mentioned Young's modulus are low-density polyethylene, linear low-density polyethylene, ultra low-density polyethylene, ethylene-vinyl acetate copolymer, ethyleneacrylate copolymer and ethylene-methacrylate copolymer, among which those considered preferable are the ethylene-vinyl acetate copolymers having a vinyl acetate content of 5 to 45 wt %, more preferably 10 to 30 wt %, ethylene-acrylate copolymer having an acrylate content of 5 to 45 wt %, more preferably 10 to 30 wt % and ethylene-methacrylate copolymer having a methacrylate content of 5 to 45 wt %, more preferably 10 to 30 wt %. These resins may be added as necessary with a slipping agent and antiblocking agent for polyolefin. In the case where the content of vinyl acetate, acrylate or methacrylate in the ethylene-vinyl acetate copolymer, ethylene-acrylate copolymer or ethylene methacrylate copolymer respectively is less than 5 wt %, the flexibility of the multilayered film obtained is somewhat insufficient; and where the above content exceeds 45 wt %, the slipping property of the obtained multilayered film is poor and cannot become satisfactory even by the addition of a slipping agent and antiblocking agent.

Hereinbelow, the present invention is further illustrated by reference to Examples, which are by no means limiting of the invention.

EXAMPLE 1

A multilayered film comprising 3 kinds and 5 layers and having a total thickness of 70μ was prepared by co-extrusion using 3 extruders and a 3-kind 5-layer multi-diehead in the following way. For the intermediate layer having a thickness of 10μ there was used an EVOH having an ethylene content of 32 mol %, a saponification degree of 99% and a melt index measured at 190° C. under a load of 2160 g according to ASTM D1238-65T (hereinafter referred to as MI) of 4.5 g/10 min. For the surface layers each having a thickness of 25μ provided on both sides of the gas barrier layer there was used a composition containing 100 parts by weight of low-density polyethylene and 1 part by weight of trimellitic acid, and the resulting surface layers each had a single-layer Young's modulus of 1.9 kg/mm$^2$. The pellets of the composition had previously been obtained by blending through an extruder and used for the surface layer. Between the intermediate layer and the surface layers were provided adhesive layers each having a thickness of 5μ, comprising a modified polyethylene modified with 0.5 wt % of maleic anhydride.

The multilayered film obtained above was evaluated for surface appearance, oxygen gas transmission rate (OTR), odor barrier property, flexibility, feeling to the wearer when worn and noise generation. The oxygen gas transmission rate was measured at 20° C. and 65% relative humidity by using OX-TRAN 10-50A available from Modern Control. A bag was prepared, for the evaluation of the other properties, by laminating two sheets of the multilayered film each having a size of 140 mm×300 mm and heat sealing zone of the 140-mm edges and two 300-mm edges each by 5-mm width. For the evaluation of the odor barrier property, the bag was charged with odorous materials in a room the atmosphere of which had been controlled to 20° C., 65% RH, and then tightly sealed by heat sealing, and the bag with the contents was placed in a wide-neck bottle, which was then stoppered and allowed to stand at 20° C., 65% RH for 24 hours. The odor in the wide-neck bottle was then evaluated by an organoleptic test with a 5-point rating. For the odorous materials, 1 g of skatole and 5 cc of 2.5% aqueous ammonia solution were used. The flexibility, the feeling when worn and the noise generation were evaluated with the bag actually worn on the belly, by the following 5-point ratings.

| Item | 5 points | 3 points | 1 point |
| --- | --- | --- | --- |
| Odor Barrier Property | No Odor At All | Same Odor | Odor |
| Flexibility | Very Flexible | Some Flexibility | Rigid |
| Feeling When Worn | Comfortable | Some Discomfort | Uncomfortable |
| Noise Generation | Almost no noise | Some noise | Significant noise |

As apparent from the evaluation results shown in Table 1, the film had excellent surface appearance and odor barrier.

EXAMPLE 2

A multilayered film comprising 3 kinds and 5 layers and having a total thickness of 70μ was prepared by co-extrusion using 3 extruders and a 3-kind 5-layer multi-diehead in the following way. For the intermediate layer having a thickness of 10μ a polymer blend was used comprising 80 parts by weight of an EVOH having an ethylene content of 32 mol %, a saponification degree of 99% and an MI of 4.5 g/10 min and 20 parts by weight of an ethylene-vinyl acetate copolymer having an ethylene content of 89 mol %, vinyl acetate content of 11 mol % and an MI of 6.0 g/10 min. For the surface layers each having a thickness of 25μ provided on both sides of the intermediate layer was used a composition containing 100 parts by weight of an ethylene-vinyl acetate copolymer having a vinyl acetate content of 28 wt % and 1 part by weight of trimellitic acid. Between the intermediate layer and the surface layers were provided adhesive layers each having a thickness of 5μ, comprising a modified ethylene-vinyl acetate copolymer modified with 0.5 wt % of maleic anhydride. The pellets of the corresponding compositions had previously been obtained by blending through an extruder and used for the intermediate layer and the surface layer. A 50-μ thick film obtained by extruding the composition for the surface layer through a single-screw extruder showed a Young's modulus of 0.5 kg/mm². The thus obtained multilayer film was evaluated in the same manner as in Example 1 and the results are shown in Table 1. As seen from the table, the film had an excellent odor barrier property, and also excellent flexibility, feeling when worn and noise prevention property.

EXAMPLE 3

Master pellets were obtained by extruding 90 parts by weight of an ethylene-vinyl acetate copolymer having a vinyl acetate content of 28 wt % and 10 parts by weight of zeolite through a twin-screw extruder and pelletizing the extruded melts. The master pellets provided a single-layer film having a Young's modulus of 0.5 kg/mm².

Next, a multilayered film comprising 3 kinds and 5 layers and having a total thickness of 70μ was prepared by co-extrusion using 3 extruders and a 3-kind 5-layer multi-diehead in the following way. For the intermediate layer having a thickness of 10μ then was used a polymer blend comprised of 70 parts by weight of an EVOH having an ethylene content of 38 mol %, a saponification degree of 99% and an MI of 1.7 g/10 min and 30 parts by weight of an ethylene-vinyl acetate copolymer having an ethylene content of 89 mol %, vinyl acetate content of 11 mol % and an MI of 2.3 g/10 min. For the surface layers each having a thickness of 25μ provided on both sides of the gas barrier layer there was used a composition containing 90 parts by weight of an ethylenevinyl acetate copolymer having a vinyl acetate content of 28 wt % and 10 parts by weight of the master pellets obtained above. Between the intermediate layer and the surface layers there were provided adhesive layers each having a thickness of 5μ, comprising a maleic-anhydride modified ethylenevinyl acetate copolymer having a vinyl acetate content of 20 wt % and a maleic anhydride content of 0.5 wt %. The pellets previously blended through an extruder were used for the intermediate layer, and those dry blended were used for the surface layer.

The multilayered film thus obtained was evaluated in the same manner as in Example 1 and the results are shown in Table 1. As is apparent from the table, the film showed an excellent surface appearance and odor barrier property, and also an excellent flexibility, feeling when worn and noise prevention.

EXAMPLE 4

Pellets were obtained by blending 99 parts by weight of low-density polyethylene and 1 part by weight of trimellitic acid, and they were formed into a single-layer film having a thickness of 50μ. A multilayered film was obtained by laminating the thus obtained film with a polyvinylidene chloride film having a thickness of 20μ by dry lamination using a 2-part cure type polyester adhesive. The obtained film was formed into a bag with the low-density polyethylene side being heat sealed. The bag was evaluated in the same manner as in Example 1 and the results are shown in Table 1. As is apparent from Table 1, the film was good both in surface appearance and odor barrier property.

EXAMPLE 5

A solution was prepared by dissolving in 360 g of water 140 g of ferrous sulfate 7 hydrates and 0.9 g of L-ascorbic acid, and further 0.2 g of alum. The solution was sprayed at conditions of liquid feed rate of 40 ml/min, spraying air rate of 15 l/min, dry air flow rate of 6 m²/min and inlet and outlet temperatures of 120° C. and 75° C. respectively to give a composition containing powdered iron (II) and ascorbic acid.

Master pellets of iron (II)-ascorbic acid composition were obtained by extruding through a twin-screw extruder 90 parts by weight of an ethylene-vinyl acetate copolymer having a vinyl acetate content of 28 wt % and 10 parts by weight of the iron (II)-ascorbic acid composition obtained above.

A multilayered film comprising 3 kinds and 5 layers and having a total thickness of 70μ was prepared by co-extrusion using 3 extruders and a 3-kind 5-layer multi-diehead in the following way. For the intermediate layer having a thickness of 10μ, there was used an EVOH having an ethylene content of 44 mol %, a saponification degree of 99% and an MI of 5.5 g/10 min. For the surface layers each having a thickness of 25μ provided on both sides of the intermediate layer was used a composition containing 90 parts by weight of an ethylene-vinyl acetate copolymer having a vinyl acetate content of 28 wt % and 10 parts by weight of the master pellets of iron (II)-ascorbic acid composition obtained above. Between the intermediate layer and the surface layers there were provided adhesive layers each having a thickness of 5μ, comprising a maleic-anhydride modified ethylene-vinyl acetate copolymer having a vinyl acetate content of 20 wt % and a maleic anhydride content of 0.5 wt %. The thus obtained multilayered film was evaluated in the same manner as in Example 1 and the results are shown in Table 1. As seen from the table, the film was good in surface appearance, odor barrier property, flexibility, feeling when worn and noise prevention property.

EXAMPLE 6

Master pellets of zinc silicate were obtained by pelletizing through a twin-screw extruder 70 parts by weight of an ethylene-vinyl acetate copolymer having a vinyl acetate content of 28 wt % and 30 parts by weight of an amorphous particulate zinc silicate having a zinc oxide-silicon oxide ratio by weight of 1:3 and an average particle size of not more than 5μ.

A multilayered film comprising 3 kinds and 5 layers and having a total thickness of 70μ, was prepared by co-extrusion using 3 extruders and a 3-kind 5-layer multi-diehead in the following way. For the intermediate layer having a thickness of 10μ there was used a composition containing 80 parts by weight of an EVOH having an ethylene content of 32 mol %, a saponification degree of 99% and an MI of 4.5 g/10 min and 20 parts by weight of an ethylene-vinyl acetate copolymer having an ethylene content of 89 mol %, vinyl acetate content of 11 mol % and an MI of 6.0 g/10 min. For the surface layers each having a thickness of 25μ provided on both sides of the intermediate layer there was used a blend composition containing 90 parts by weight of an ethylene-vinyl acetate copolymer having a vinyl acetate content of 28 wt % and 10 parts by weight of the master pellets of zinc silicate obtained above. Between the intermediate layer and the surface layers were provided adhesive layers, each having a thickness of 5μ, comprising a maleic-anhydride modified ethylene-vinyl acetate copolymer having a vinyl acetate content of 20 wt % and a maleic anhydride content of 0.5 wt %. The pellets previously blended through an extruder were used for the intermediate layer, and those dry blended were used for the surface layer. The thus obtained multilayered film was evaluated in the same manner as in Example 1 and the results are shown in Table 1. As seen from the table, the film was excellent in surface appearance and odor barrier property, as well as in flexibility, feeling when worn and noise prevention property.

EXAMPLE 7

Example 6 was repeated except for using fine particles having an average particle size of not more than 10μ of a composition comprising zinc oxide and alum in a weight ratio of 5:1 instead of the particulate zinc silicate to obtain a 3-kind 5-layer multilayered film.

The thus obtained multilayered film was evaluated in the same manner as in Example 1 and the results are shown in Table 1. As seen from the table, the film was excellent in surface appearance and odor barrier property, as well as in flexibility, feeling when worn and noise prevention property.

EXAMPLE 8

A polyvinylidene chloride resin was dissolved at 23° C. in a 2/1 by weight mixed solvent of tetrahydrofuran/toluene.

The thus obtained solution was added with a particulate zinc silicate comprised of zinc oxide and silicon oxide in a ratio by weight of 1:3 having an average particle size of not more than 5μ in an amount such of 3 wt % based on the weight of the dissolved polyvinylidene chloride resin, and the mixture was, after being mixed with vigorous stirring, cast into a single-layer film of polyvinylidene chloride having a thickness of 10μ.

A multilayered film was obtained by dry laminating films each having a thickness of 30μ obtained by extruding through a single-screw extruder an ethylene-vinyl acetate copolymer having a vinyl acetate content of 28 wt % on both sides of the polyvinylidene chloride film obtained above using a 2-part polyester adhesive.

The thus obtained multilayered film was evaluated in the same manner as in Example 1 and the results are shown in Table 1. As seen from the table, the film was excellent in surface appearance and odor barrier property, and was good in flexibility, feeling when worn and noise prevention property.

EXAMPLE 9

An EVOH having an ethylene content of 32 mol %, a saponification degree of 99% and an MI of 4.5 g/10 min was dissolved at 20° C. in a 65/35 by weight mixed solvent of n-propanol/water.

The thus obtained solution was added with fine particles of a mixture of zinc oxide and alum in a ratio by weight of 5:1 having an average particle size of not more than 10μ in an amount of 3 wt % based on the weight of the EVOH, and the mixture was, after being mixed with vigorous stirring, cast into a single-layer film of EVOH having a thickness of 10μ.

A multilayered film was obtained, in the same manner as in Example 8, by dry laminating the films each having a thickness of 30μ of the ethylene-vinyl acetate copolymer on both sides of the EVOH film obtained above using a 2-part polyester adhesive.

The thus obtained multilayered film was evaluated in the same manner as in Example 1 and the results are shown in Table 1. As seen from the table, the film was excellent in surface appearance and odor barrier property, and was good in flexibility, feeling when worn and noise prevention property.

EXAMPLE 10

A multilayered film comprising 3 kinds and 5 layers and having a total thickness of 70μ was prepared by co-extrusion using 3 extruders and a 3-kind 5-layer multi-diehead in the following way. For the intermediate layer having a thickness of 10μ there was used a polymer blend comprised of 70 parts by weight of an EVOH having an ethylene content of 32 mol %, a saponification degree of 99% and an MI of 4.5 g/10 min, 20 parts by weight of an ethylene-vinyl acetate copolymer having an ethylene content of 89 mol %, vinyl acetate content of 11 mol % and an MI of 6.0 g/10 min and 10 parts by weight of the same master pellets of zinc silicate as used in Example 6. For the surface layers each having a thickness of 25μ provided on both sides of the intermediate layer was used an ethylene-vinyl acetate copolymer having a vinyl acetate content of 28 wt %. Between the intermediate layer there and the surface layers were provided adhesive layers each having a thickness of 5μ, comprising a maleic-anhydride modified ethylene-vinyl acetate copolymer having a vinyl acetate content of 20 wt % and a maleic anhydride content of 0.5 wt %. For the intermediate layer, the pellets previously obtained by blending the composition through an extruder were used.

The thus obtained multilayered film was evaluated in the same manner as in Example 1 and the results are shown in Table 1. As seen from the table, the film was excellent in surface appearance and odor barrier property, and was good in flexibility, feeling when worn and noise prevention property.

EXAMPLE 11

Example 10 was repeated except that a composition comprised of 90 parts by weight of ethylene-vinyl acetate copolymer having a vinyl acetate content of 28 wt % and 10 parts by weight of the same master pellets of zinc silicate as used in Example 6 was used for the surface layer having a thickness of 25μ to obtain a multilayered film.

The thus obtained multilayered film was evaluated in the same manner as in Example 1 and the results are shown in Table 1. As seen from the table, the film was excellent in surface appearance and odor barrier property, and was good in flexibility, feeling when worn and noise prevention property.

Comparative Example 1

A multilayered film comprising 3 kinds and 5 layers and having a total thickness of 70μ was prepared by co-extrusion using 3 extruders and a 3-kind 5-layer multi-diehead in the following way. For the intermediate layer having a thickness of 10μ there was used a polymer blend comprised of 80 parts by weight of an EVOH having an ethylene content of 32 mol %, a saponification degree of 99% and an MI of 4.5 g/10 min and 20 parts by weight of an ethylene-vinyl acetate copolymer having an ethylene content of 89 mol %, vinyl acetate content of 11 mol % and an MI of 6.0 g/10 min. For the surface layers each having a thickness of 25μ provided on both sides of the intermediate layer there was used an ethylene-vinyl acetate copolymer having a vinyl acetate content of 28 wt %. Between the intermediate layer and the surface layers were provided adhesive layers each having a thickness of 5µ, comprising a maleic-anhydride modified ethylene-vinyl acetate copolymer having a vinyl acetate content of 20 wt % and a maleic anhydride content of 0.5 wt %. For the intermediate layer, the pellets previously obtained by blending the composition through an extruder were used.

The thus obtained multilayered film was evaluated in the same manner as in Example 1 and the results are shown in Table 1. As seen from the table, the film had an insufficient odor barrier property.

Comparative Example 5

A single-layer film having a thickness of 70µ was obtained from an ethylene-vinyl acetate copolymer having a vinyl acetate content of 28 wt % by using a single-screw extruder.

The thus obtained film was evaluated in the same manner as in Example 1 and the results are shown in Table 1. As seen from the table, the film had a poor odor barrier property.

TABLE 1

|  | Film surface appearance | OTR cc/ ($m^2 \cdot day \cdot atm$) | Evaluation |  |  |  |  |
|---|---|---|---|---|---|---|---|
|  |  |  | Performances in pratice |  |  |  |  |
|  |  |  | Odor barrier |  | Feeling |  |  |
|  |  |  | skatole | ammonia | Flexibility | when worn | noise generation |
| Example 1 | good | 0.7 | 5 | 5 | 3 | 3 | 3 |
| Example 2 | good | 0.9 | 5 | 5 | 5 | 5 | 5 |
| Example 3 | good | 1.2 | 5 | 5 | 5 | 5 | 5 |
| Example 4 | good | 6.2 | 3 | 4 | 3 | 3 | 3 |
| Example 5 | good | 2.3 | 5 | 5 | 3 | 3 | 3 |
| Example 6 | good | 0.9 | 5 | 5 | 5 | 5 | 5 |
| Example 7 | good | 0.9 | 5 | 5 | 5 | 5 | 5 |
| Example 8 | good | 6.2 | 3 | 4 | 3 | 3 | 3 |
| Example 9 | good | 0.7 | 5 | 5 | 3 | 3 | 3 |
| Example 10 | good | 0.9 | 5 | 5 | 4 | 4 | 4 |
| Example 11 | good | 0.9 | 5 | 5 | 4 | 4 | 4 |
| Comp. Ex. 1 | good | 0.9 | 5 | 1 | 5 | 5 | 5 |
| Comp. Ex. 2 | good | 0.9 | 5 | 1 | 3 | 3 | 3 |
| Comp. Ex. 3 | good | 6.2 | 2 | 2 | 3 | 3 | 3 |
| Comp. Ex. 4 | good | more than 2000 | 1 | 3 | 5 | 5 | 5 |
| Comp. Ex. 5 | good | more than | 1 | 1 | 5 | 5 | 5 |

Comparative Example 2

The same EVOH as used in Example 9 was formed into a single-layer film through a single-screw extruder. Example 9 was repeated except for using the thus obtained film as the intermediate layer to obtain a 3-kind 5-layer multi-layered film by dry lamination.

The thus obtained multilayered film was evaluated in the same manner as in Example 1 and the results are shown in Table 1. As seen from the table, the film had an insufficient odor barrier property.

Comparative Example 3

A polyvinylidene chloride film was obtained through a single-screw extruder. Example 8 was repeated except for using the thus obtained film as the intermediate layer to obtain a 3-kind 5-layer multilayered film by dry lamination.

The thus obtained multilayered film was evaluated in the same manner as in Example 1 and the results are shown in Table 1. As seen from the table, the film had an insufficient odor barrier property.

Comparative Example 4

Blend pellets were obtained from 90 parts by weight of an ethylene-vinyl acetate copolymer having a vinyl acetate content of 28 wt % and 1 part by weight of trimellitic acid. The blend pellets were formed into a single-layer film having a thickness of 70µ through a single-screw extruder.

The thus obtained film was evaluated in the same manner as in Example 1 and the results are shown in Table 1. As seen from the table, the film had an insufficient odor barrier property.

The multilayered structure, particularly the multilayered film, of the present invention exhibits excellent barrier properties against odorous materials, and is hence useful as a colostomy bag, and further as odor barrier materials for packaging odorous wastes such as garbage, and packages for fish, fruits, vegetables and the like, and for corpses or the like.

We claim:

1. A multilayered structure consisting essentially of at least one gas barrier layer of an ethylene-vinyl alcohol copolymer having an ethylene content of 20 to 50 mol % and an oxygen transmission rate measured at 20° C., 65% RH of not more than 10 cc. 20µ/$m^2 \cdot day \cdot atm$.; at least one protective layer to protect said gas barrier layer, and from 0.1% to 50% by weight of a deodorant incorporated in either or both of said layers, the weight % of said deodorant being based upon the weight of the layer in which said deodorant is incorporated, said multilayered structure providing an effective barrier against skatole and ammonia odors.

2. A multilayered structure as defined in claim 1 additionally containing an adhesive layer between said layers.

3. A multilayered structure as defined in claim 2 wherein said deodorant is incorporated in one or more of said gas barrier, protective and/or adhesive layers.

4. A multilayered structure as defined in claim 1 wherein the gas barrier layer comprises an ethylene vinyl alcohol copolymer blended with an ethylene copolymer resin containing 2 to 25 mol % of a member selected from the group consisting of vinyl acetate, acrylic acid esters, methacrylic acid esters, and mixtures thereof.

5. A multilayered structure as defined in claim 4, wherein said gas barrier layer comprises 60 to 95 parts by weight of said ethylene vinyl alcohol copolymer and 40 to 5 parts by weight of said ethylene copolymer.

6. A multilayered structure according to claim 1 wherein said deodorant is contained in said protective layer.

7. A multilayered structure according to claim 1 wherein said deodorant is a composition comprising a member selected from the group consisting of a zinc compound, an aluminum compound, a silicon compound, an iron (II) compound, and mixtures thereof.

8. A multilayered structure according to claim 1 wherein said protective layer is a thermoplastic resin layer.

9. A multilayered structure according to claim 8 wherein said thermoplastic resin layer exhibits a Young's modulus (20° C.) of not more than 2.5 kg/mm$^2$.

* * * * *